(12) United States Patent
Huang et al.

(10) Patent No.: US 10,354,422 B2
(45) Date of Patent: Jul. 16, 2019

(54) DIAGRAM BUILDING SYSTEM AND METHOD FOR A SIGNAL DATA DECOMPOSITION AND ANALYSIS

(71) Applicant: National Central University, Taoyuan (TW)

(72) Inventors: Norden E. Huang, Jhongli (TW); Bo-Jau Kuo, Taipei (TW); Yu-Cheng Lin, Taipei (TW); Chung-Kang Peng, Sharon, MA (US); Men-Tzung Lo, Jhongli (TW)

(73) Assignee: NATIONAL CENTRAL UNIVERSITY, Taoyuan County (TW)

( * ) Notice: Subject to any disclaimer, the term of this patent is extended or adjusted under 35 U.S.C. 154(b) by 51 days.

(21) Appl. No.: 15/090,100

(22) Filed: Apr. 4, 2016

(65) Prior Publication Data
US 2016/0292894 A1    Oct. 6, 2016

Related U.S. Application Data

(63) Continuation-in-part of application No. 14/273,082, filed on May 8, 2014, now abandoned.

(30) Foreign Application Priority Data

Dec. 10, 2013   (TW) .............................. 102145345 A

(51) Int. Cl.
*G06T 11/20*       (2006.01)
*A61B 5/02*        (2006.01)
(Continued)

(52) U.S. Cl.
CPC .............. *G06T 11/206* (2013.01); *A61B 5/02* (2013.01); *A61B 5/7275* (2013.01); *G06F 19/00* (2013.01); *G06T 11/001* (2013.01); *G16H 40/63* (2018.01)

(58) Field of Classification Search
CPC ...... G06T 11/001; G06T 11/206; G06F 19/00; G16H 40/63; A61B 5/02; A61B 5/7275
See application file for complete search history.

(56) References Cited

U.S. PATENT DOCUMENTS 5,577,159 A * 11/1996 Shoham .............. G10L 19/0212
                                                      704/206
6,311,130 B1 * 10/2001 Huang .................... G06F 17/14
                                                       702/15
(Continued)

*Primary Examiner* — Walter Yehl
(74) *Attorney, Agent, or Firm* — Muncy, Geissler, Olds & Lowe, P.C.

(57) ABSTRACT

The present invention provides a diagram building system adapted for processing a signal with a time period. The diagram building system comprises a inputting device for receiving the signal; a computing device, dividing the signal into a plurality of window scales according to one of time interval scales; decomposing the window scales via HHT algorithm to generate a plurality of quantized windows according to different components; then, calculating the value of quantized windows with the same single-frequency component through a quantifying function to generate a plurality of specific frequency values; an outputting device, sequentially arranging the specific frequency values according to the time interval scales and the single-frequency components to form a visual diagram.

11 Claims, 18 Drawing Sheets
(9 of 18 Drawing Sheet(s) Filed in Color)

(51) Int. Cl.
  *A61B 5/00*   (2006.01)
  *G06T 11/00*  (2006.01)
  *G16H 40/63*  (2018.01)
  *G06F 19/00*  (2018.01)

(56) References Cited

U.S. PATENT DOCUMENTS

| | | | | |
|---|---|---|---|---|
| 6,381,559 | B1* | 4/2002 | Huang | G06F 17/14 |
| | | | | 702/189 |
| 2002/0147579 | A1* | 10/2002 | Kushner | G10L 15/30 |
| | | | | 704/207 |
| 2003/0033094 | A1* | 2/2003 | Huang | G06F 17/14 |
| | | | | 702/39 |
| 2003/0105640 | A1* | 6/2003 | Chang | G11B 20/00007 |
| | | | | 704/503 |
| 2004/0078160 | A1* | 4/2004 | Frei | G06F 17/14 |
| | | | | 702/79 |
| 2005/0153267 | A1* | 7/2005 | Goldman | G09B 7/00 |
| | | | | 434/308 |
| 2010/0087747 | A1* | 4/2010 | Lo | A61B 5/0205 |
| | | | | 600/529 |
| 2010/0092028 | A1* | 4/2010 | Huang | G06F 17/14 |
| | | | | 382/100 |
| 2012/0177233 | A1* | 7/2012 | Kidmose | A61B 5/04845 |
| | | | | 381/314 |

\* cited by examiner

DIAGRAM BUILDING SYSTEM AND METHOD FOR A SIGNAL DATA DECOMPOSITION AND ANALYSIS

CROSS-REFERENCE TO RELATED APPLICATIONS

This is continuation-in-part application of U.S. application Ser. No. 14/273,082 filed on May 8, 2014, now pending, the entire disclosure of which is incorporated herein by reference.

FIELD OF THE INVENTION

The invention relates to a diagram building system and method, more particularly, to a diagram building system and method for a signal data analyzing to generate a three-dimensional variation visual diagram.

BACKGROUND OF THE INVENTION

As technology advances, more and more detectors are used to detect physiological signal, which can provide users detecting their physical condition by themselves. However, the physiological signals detected by the detectors are various and complex, and the information measured for each time cannot be collated in a systematic way. The users only can know the current physical condition, but cannot know individual overall trend toward and changes physiological parameters.

The conventional technology has provided some health management systems, but almost of them are off-line diagram building systems. The conventional health management systems are not only relatively large and complex, but also need professional human operations to analyze, so the cost is high and it requires more manpower and time consuming.

SUMMARY OF THE INVENTION

The present invention provides a diagram building adapted to process a signal data analysis, and the signal data with a time period, wherein the signal data can be a nonlinear or non-stationary data, such as physiology information. The diagram building system includes an inputting device for receiving the signal data, a computing device and an outputting device for displaying a visual diagram. The computing device further comprises a segmenting processor, an analyzing processor and a reorganizing processor.

The segmenting processor of the invention divides the signal data into a plurality of window scales according to one of time interval scales. The time interval scale is one of time periods which the signal data with.

The analyzing processor of the invention decomposes the window scales via Hilbert Huang transform (HHT) algorithm to generate a plurality of quantized windows according to different components. In a preferred embodiment, the components are composed of a plurality of single-frequency components.

The reorganizing processor of the invention respectively calculates the value of quantized windows with the same frequency component through a quantifying function to generate a plurality of specific frequency values.

Finally, the outputting device of the invention sequentially arranges the specific frequency values according to the time interval scales and the single-frequency components to form a visual diagram.

The present invention also provides a diagram building method for a signal data analyzing, that comprises receiving a signal data. The segmenting processor repeats to divide the signal data into a plurality of window scales according to one of time interval scales, wherein each time interval scale is one of time periods which the signal data with. By Hilbert-Huang Transform (HHT) algorithm, the window scales are decomposed by the analyzing processor to generate a plurality of quantized windows according to different components, wherein the components are a plurality of single-frequency components. The method further respectively calculates the value of quantized windows with the same single-frequency component through a quantifying function to generate a plurality of specific frequency values via the reorganizing processor. Finally, the outputting device is connected to the compute device and sequentially arranges the specific frequency values according to the time interval scales and the single-frequency components to form a visual diagram.

The diagram building system and method of the invention can be provided as an automated health management system through comparing the indicators generated after processing the signal data and health indicators measured. Furthermore, the signal data measured by personal health detectors can be automatically uploaded to the server via a wired connection or a wireless connection to be either directly analyzed by the server or by the individual client.

All records and information are stored and applied EMD method of Hilbert transform method to decompose the complex signal data into different components and non-oscillation trends. The components are a plurality of intrinsic mode functions (IMFs). In a preferred embodiment, the components are a plurality of single-frequency components. The non-oscillation trend is a non-oscillation residue.

The intrinsic mode functions (IMFs) decomposed can be as fluctuations information of physiological parameters in these days, weeks or months. The non-oscillation residue has ruled out the influence of the transient noise or temporary fluctuations, therefore the non-oscillation residue can be used as individual overall trend toward and changes physiological parameters, so that users can effectively get their physical condition and related information.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

For clarity of disclosure, and not by way of limitation, the detailed description of the invention is divided into the subsections that follow. The present invention provides merely an example of the different types of functional arrangements that may be employed to implement the operation in the various components of a system, such as a computer connected to a detector, a multiprocessor computing device, and so forth.

For example, a physiology data may be detected by an ECG/EKG device, and the computer connecting with the ECG/EKG device implement the present invention analyzing to form a visual diagram of physiology data, then showing the visual diagram on a screen. For another example, a mechanical noise data may be detected by a vibration analyzer, and the computer connecting with the vibration analyzer implement the present invention analyzing to form a visual diagram of mechanical noise data, then printing the visual diagram by a printer. There is no limit for the implementation of diagram building system in this invention.

The segmenting processor 210, analyzing processor 220, re-organizing processor 230, and outputting device 240 can each be application specific integrated circuits or computer processors or field-programmable gate arrays (FPGA), or dedicated server processing threads. Likewise, the database can comprise any of the non-volatile memory types available for storing data variables.

The method execution steps of the present invention may include application specific software which may store in any portion or component of the memory including, such as random access memory (RAM), read-only memory (ROM), hard drive, solid-state drive, magneto optical (MO), IC chip, USB flash drive, memory card, optical disc such as compact disc (CD) or digital versatile disc (DVD), floppy disk, magnetic tape, or other memory components.

Figure 1:
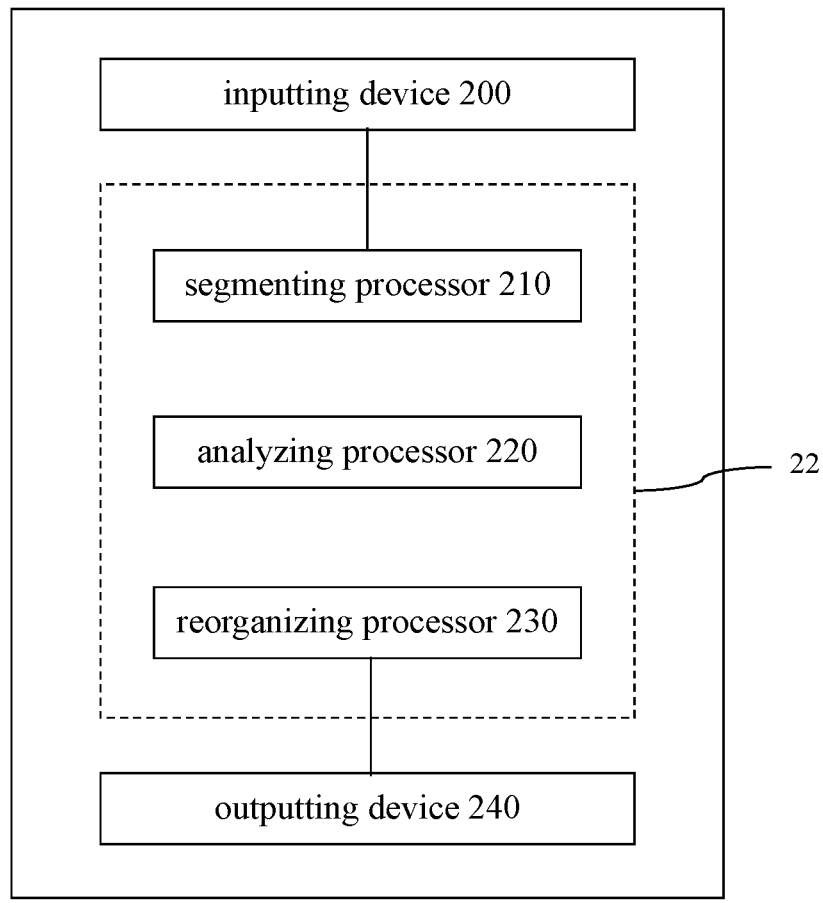
FIG. 1 shows a diagram of the diagram building system in the invention.

Please refer to FIG. 1 showing a diagram of the diagram building system in the invention. The diagram building system 20 is adapted to process a signal data TS, and the signal data TS includes a time period T. The diagram building system 20 includes an inputting device 200 for receiving the signal data TS. The signal data can be a nonlinear or non-stationary data, such as physiology information.

The diagram building system 20 further comprises an inputting device 200 for receiving a signal data, a computing device 22 and an outputting device 240 for displaying a visual diagram, for example, a three-dimensional variation visual diagram. The computing device 22 includes a segmenting processor 210, an analyzing processor 220 and a reorganizing processor 230. The compute device 22 is a remote device or a proximal device. The visual diagram is the relationship of specific frequency value between a window scale domain and a time domain. The relationship of specific frequency value is a three-dimensional color-level-variation visual diagram with a triangular form. The outputting device 240 is a command line interface (CLI) or a graphical user interface (GUI) provided in the operating interface 241.

Figure 2:
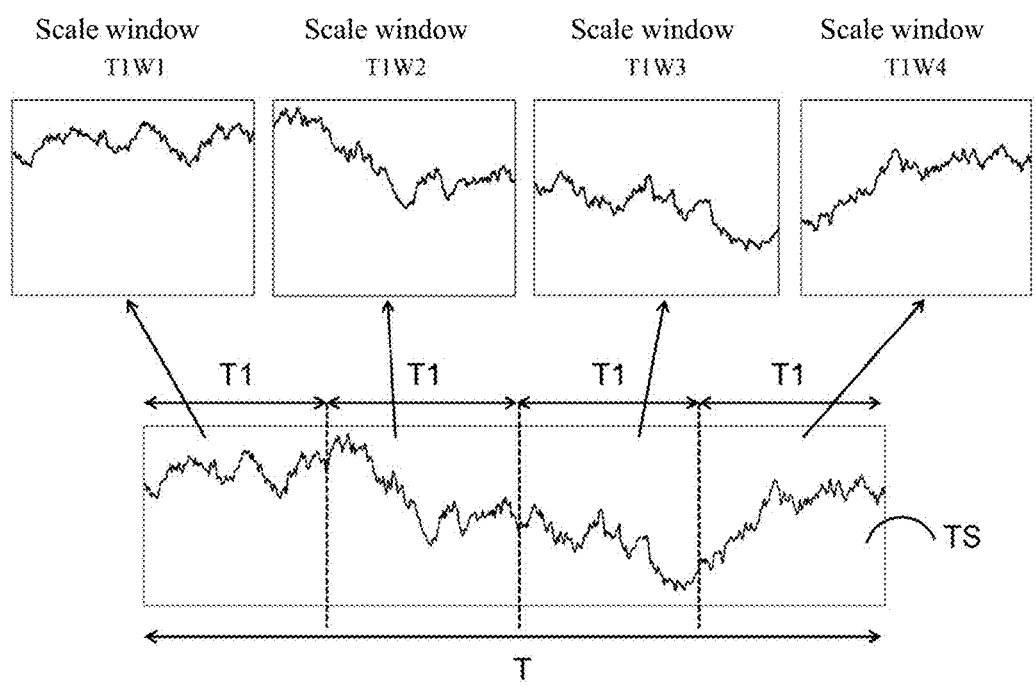
FIG. 2 shows a diagram of a first embodiment of the signal segmented in the invention.
Figure 3A:
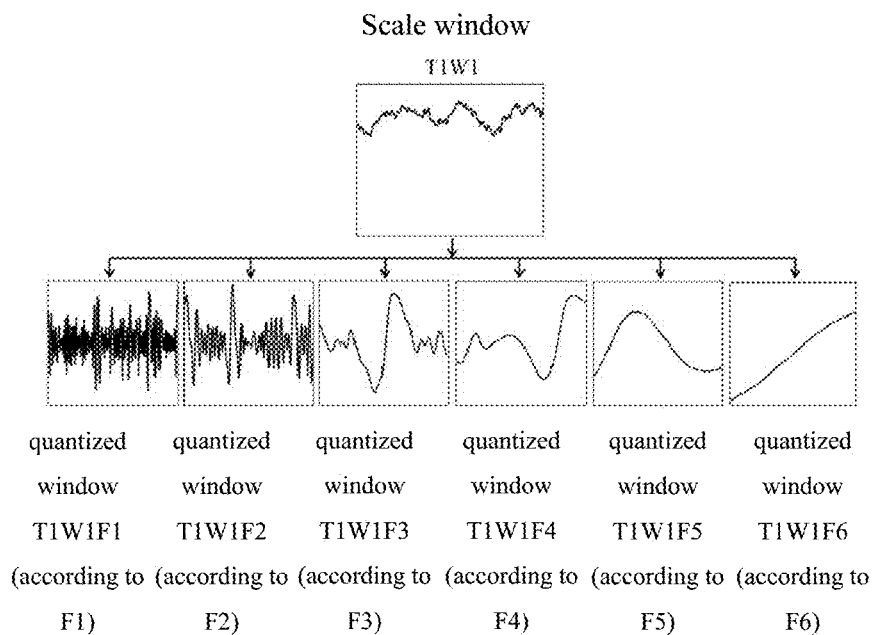
FIG. 3A to FIG. 3D respectively show diagrams of the window scale generating a plurality of quantized windows according to different components in the invention.
Figure 3B:
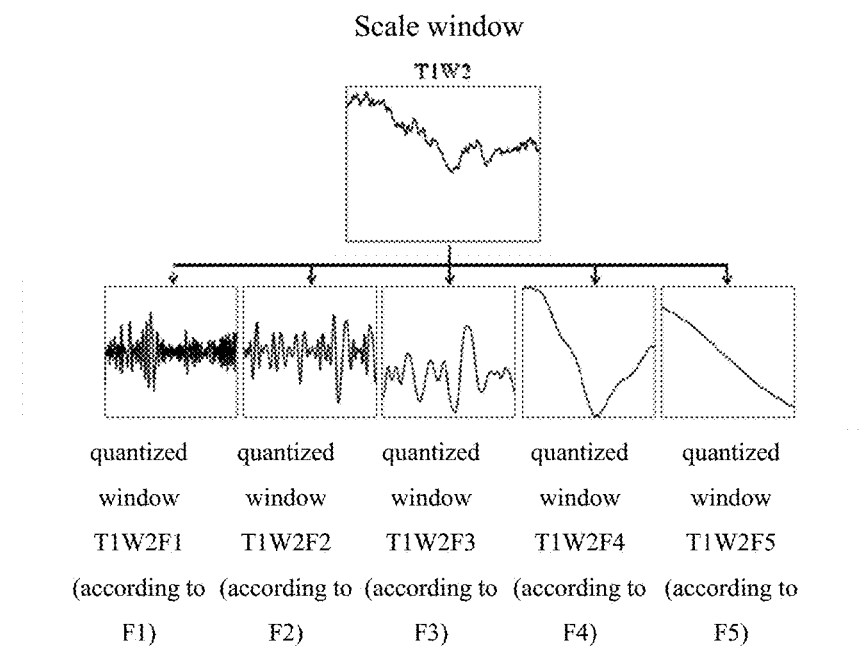
Figure 3C:
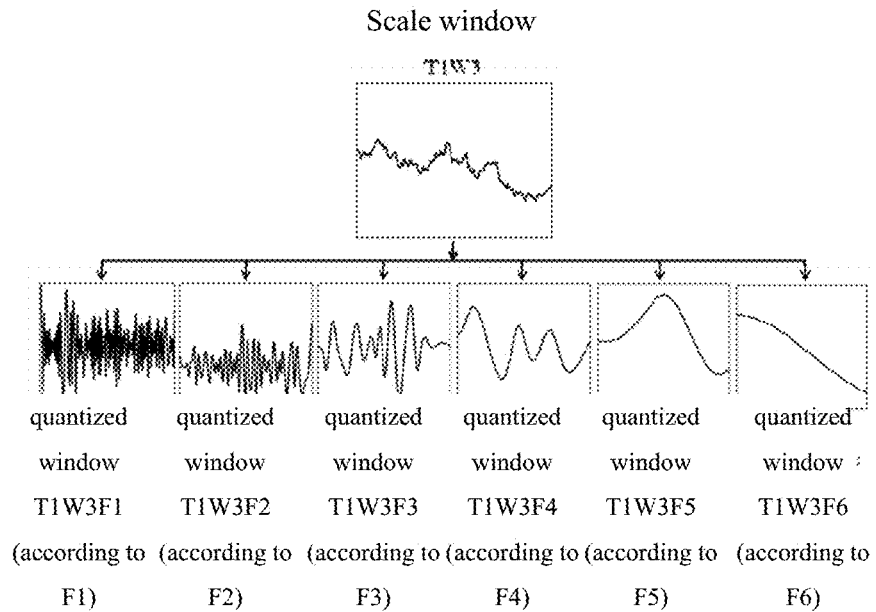
Figure 3D:
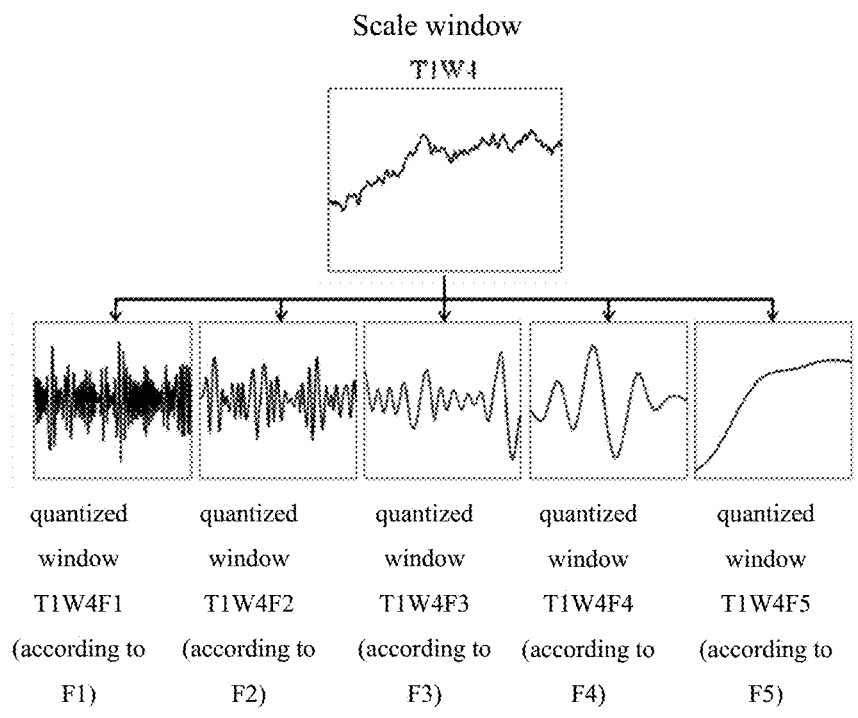

Please refer to FIG. 2 showing a diagram of a first embodiment of the signal segmented in the invention. The segmenting processor 210 of the invention divides the signal data TS into a plurality of window scales according to one of time interval scales, wherein each time interval scale is one of time periods which the signal data with. In an embodiment, when the time period T is 600 seconds and the time interval scale T1 is 20 seconds, the signal data TS is divided into 30 window scales by the segmenting processor 210. When the time interval scale T1 is 40 seconds, the signal data TS is divided into 15 window scales, which is not limited herein.

Please refer to FIG. 2, in order to clearly describe the features of the invention, the signal data TS being divided into 4 window scales by the segmenting processor 210 based on the time interval scale T1 is taken as an example. The 4 window scales are respectively a window scale T1W1, a window scale T1W2, a window scale T1W3 and a window scale T1W4, which is not limited herein.

The analyzing processor 220 of the invention repeats to decompose the window scales by Hilbert-Huang Transform (HHT) algorithm to generate a plurality of quantized windows according to different components, wherein the components are a plurality of single-frequency components. In a preferred embodiment, the HHT algorithm comprises an Empirical Mode Decomposition (EMD) methods, and the single-frequency components are a plurality of intrinsic mode functions (IMF) and a trend function.

Please refer to FIG. 3A to FIG. 3D respectively showing diagrams of the window scale generating a plurality of quantized windows according to different components in the invention. As above embodiment, the window scale T1W1, the window scale T1W2, the window scale T1W3 and the window scale T1W4 are respectively decomposed by the analyzing processor 220 to generate a plurality of quantized windows according to a first component F1, a second component F2, and a third component F3.

For example, the window scale T1W1 is decomposed by the analyzing processor 220 to generate a quantized window T1W1F1, a quantized window T1W1F2 and a quantized window T1W1F3 according to the three different components. The window scale T1W2 is decomposed by the analyzing processor 220 to generate a quantized window T1W2F1, a quantized window T1W2F2 and a quantized window T1W2F3 according to the three different components, which is not limited herein.

The reorganizing processor 230 of the invention respectively calculates the value of quantized windows with the same single-component through a quantifying function to generate a plurality of specific frequency values.

Figure 4A:
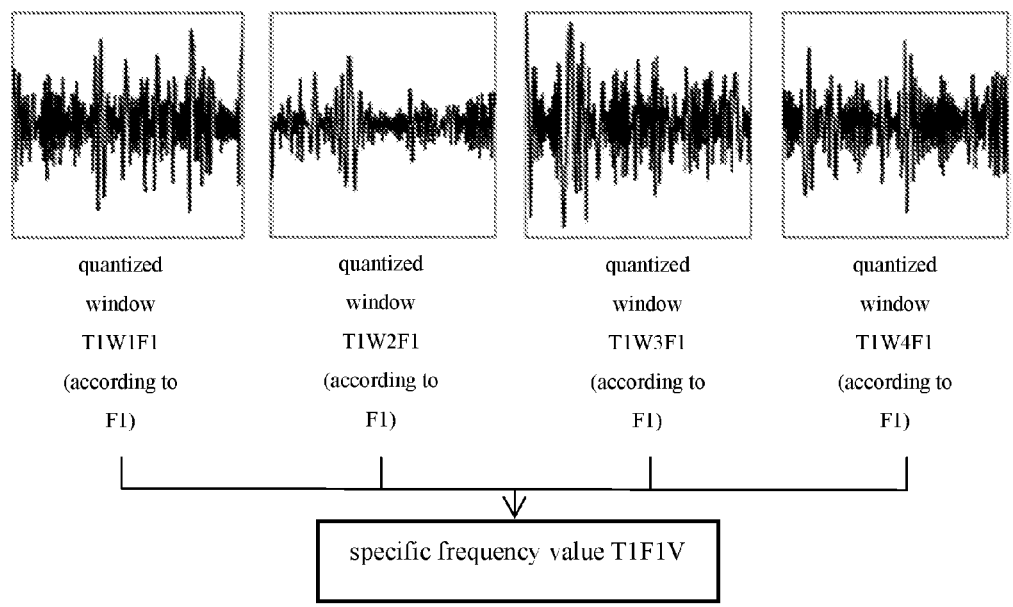
FIG. 4A to FIG. 4C respectively show diagrams of the quantized windows with the same component being reorganized to generate a plurality of specific frequency values.
Figure 4B:
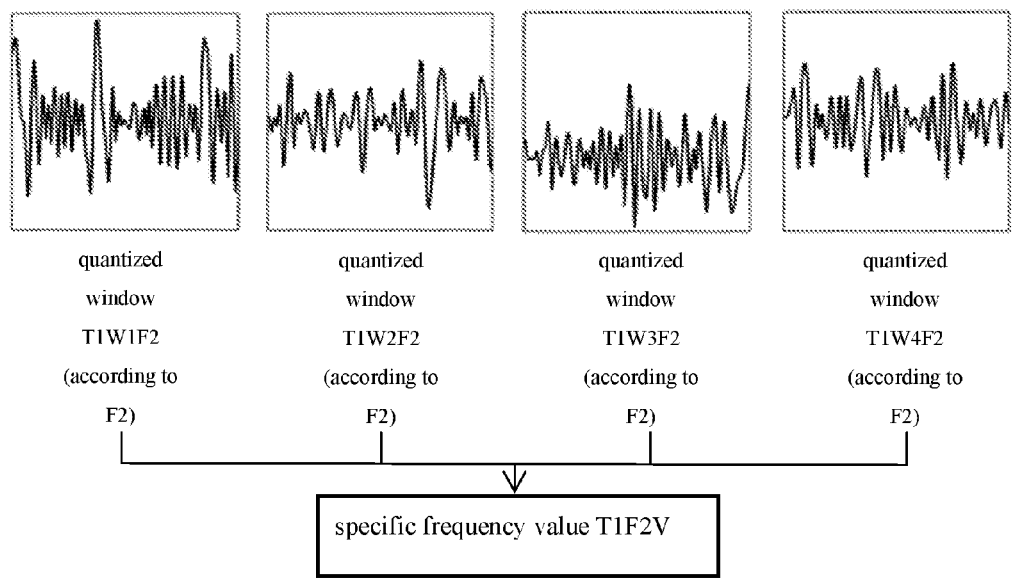
Figure 4C:
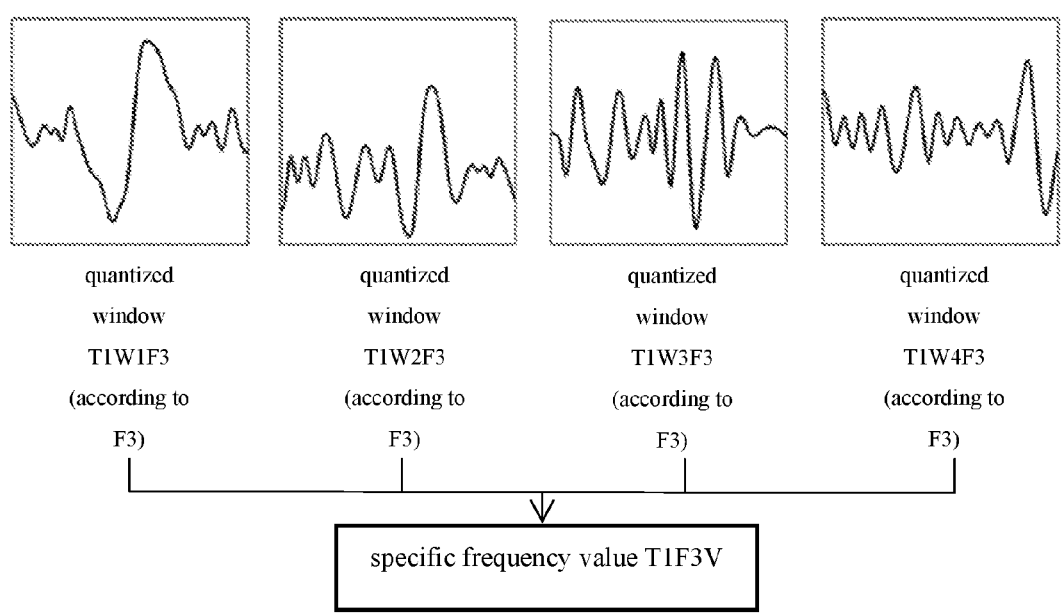

Please refer to FIG. 4A to FIG. 4C respectively showing diagrams of the quantized windows with the same component being calculated through a quantifying function to generate a plurality of specific frequency values. As above embodiment, in the situation based on the first component F1 to calculate the value of quantized windows through a quantifying function by the reorganizing processor 230 to generate a specific frequency values, a quantized window T1W1F1, a quantized window T1W2F1, a quantized window T1W3F1, and a quantized window T1W4F1 are selected from the quantized windows (the window scale T1W1, the window scale T1W2, the window scale T1W3 and the window scale T1W4) with the first component F1 to calculate and further to generate a specific frequency value T1F1V.

In the situation based on the second component F2 to calculate the value of quantized windows through a quantifying function by the reorganizing processor 230 to generate the specific frequency values, a quantized window T1W1F2, a quantized window T1W2F2, a quantized window T1W3F2, and a quantized window T1W4F2 are selected from the quantized windows (the window scale T1W1, the window scale T1W2, the window scale T1W3 and the window scale T1W4) with the second component F2 to calculate and further to generate a specific frequency value T1F2V, which is not limited herein. The quantifying function is a standard deviation function, a value difference function, a value slope function or a fluctuation index function.

Figure 5:
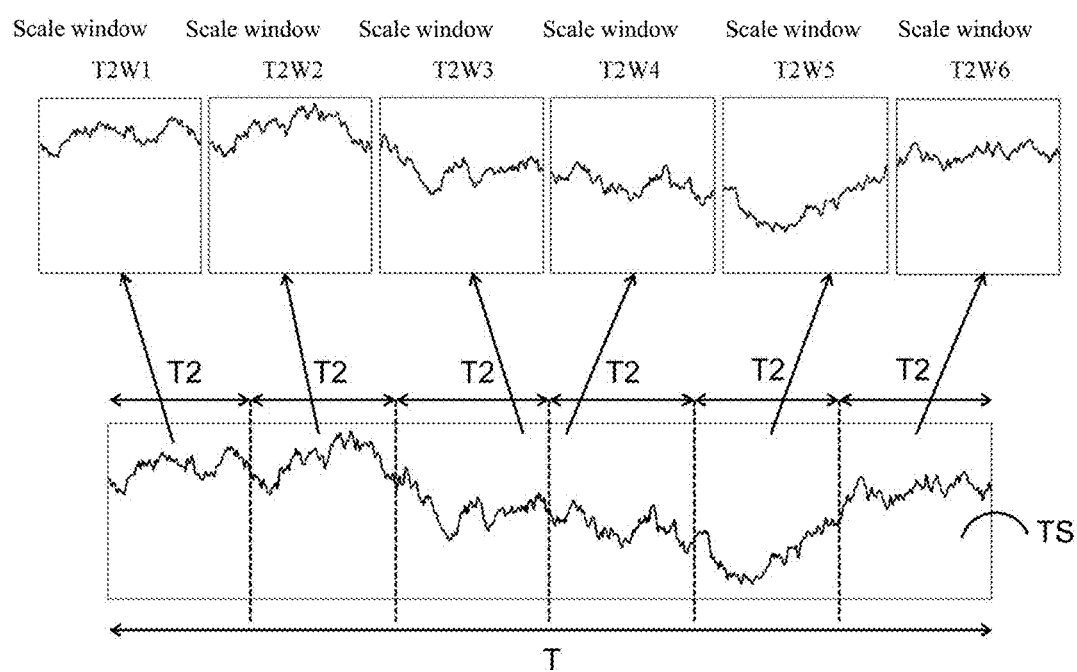
FIG. 5 shows a diagram of a second embodiment of the signal segmented in the invention.

In another embodiment, please refer to FIG. 5 showing a diagram of a second embodiment of the signal segmented in the invention. The segmenting processor 210 dividing the signal data TS into 6 window scales according to the time interval scale T2 is taken as an example. The 6 window scales are respectively a window scale T2W1, a window scale T2W2, a window scale T2W3, a window scale T2W4, a window scale T2W5, and a window scale T2W6, which is not limited herein.

The analyzing processor 220 repeats to decompose the window scale T2W1, the window scale T2W2, the window scale T2W3, the window scale T2W4, the window scale T2W5, and the window scale T2W6 by HHT algorithm to generate the quantized windows (T2W1F1, T2W1F2, T2W1F3, T2W1F4; T2W2F1, T2W2F2, T2W2F3, T2W2F4; T2W3F1, T2W3F2, T2W3F3, T2W3F4; T2W4F1, T2W4F2, T2W4F3, T2W4F4; T2W5F1, T2W5F2, T2W5F3, T2W5F4; T2W6F1, T2W6F2, T2W6F3, T2W6F4) respectively according to the first component F1, the second component F2, the third component F3, and the fourth component F4, which is not limited herein.

The reorganizing processor 230 respectively calculates the value of quantized windows according to the first component F1, the second component F2, the third component F3, and the fourth component F4 through a quantifying function to generate a plurality of specific frequency values (T2F1V, T2F2V, T2F3V, T2F4V), wherein the quantifying function is a standard deviation function, a value difference function, a value slope function or a fluctuation index function, which is not limited herein.

Finally, the outputting device 240 of the invention is connected to the compute device, sequentially arranges the specific frequency values according to the time interval scales and the single-frequency components to form a visual diagram.

Figure 6:
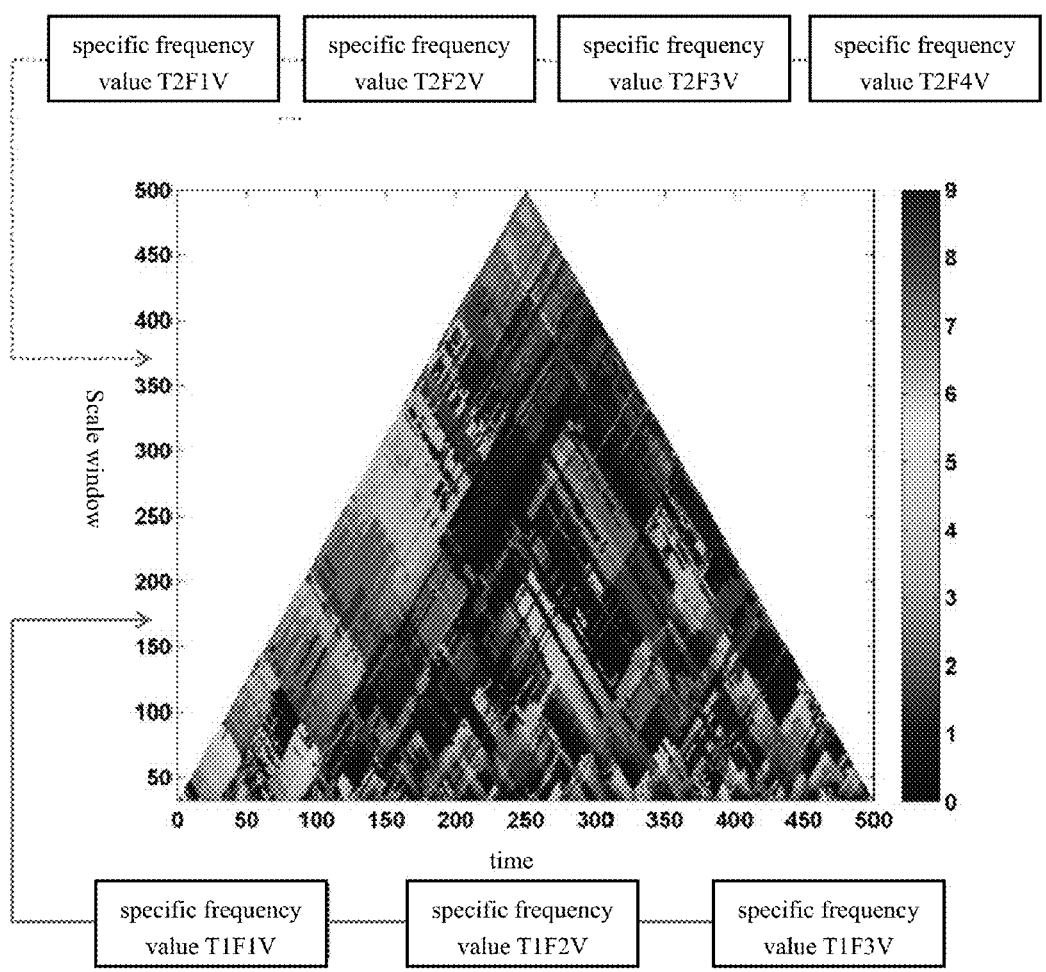
FIG. 6 shows a three-dimensional variation visual diagram of accumulating the specific frequency values of the first embodiment and the second embodiment of the invention.

Please refer to FIG. 6 showing a visual diagram of arranging the specific frequency values of the first embodiment and the second embodiment of the invention. The visual diagram is the relationship of specific frequency value between a window scale domain and a time domain. The relationship of specific frequency value is a three-dimensional color-level-variation visual diagram with a triangular form. The visual diagram is the relationship of between a window scale domain and a fluctuation index domain.

As above embodiment, the outputting device 240 arranges the specific frequency values T1F1V, T1F2V and T1F3V of the first embodiment and the specific frequency values T2F1V, T2F2V, T2F3V, and T2F4V of the second embodiment according to the time interval scales and the single-frequency components to form the three-dimensional variation visual diagram, wherein each specific frequency value is represented by time interval scale (widow scale) and single-frequency component (time f=1/t).

Figure 7:
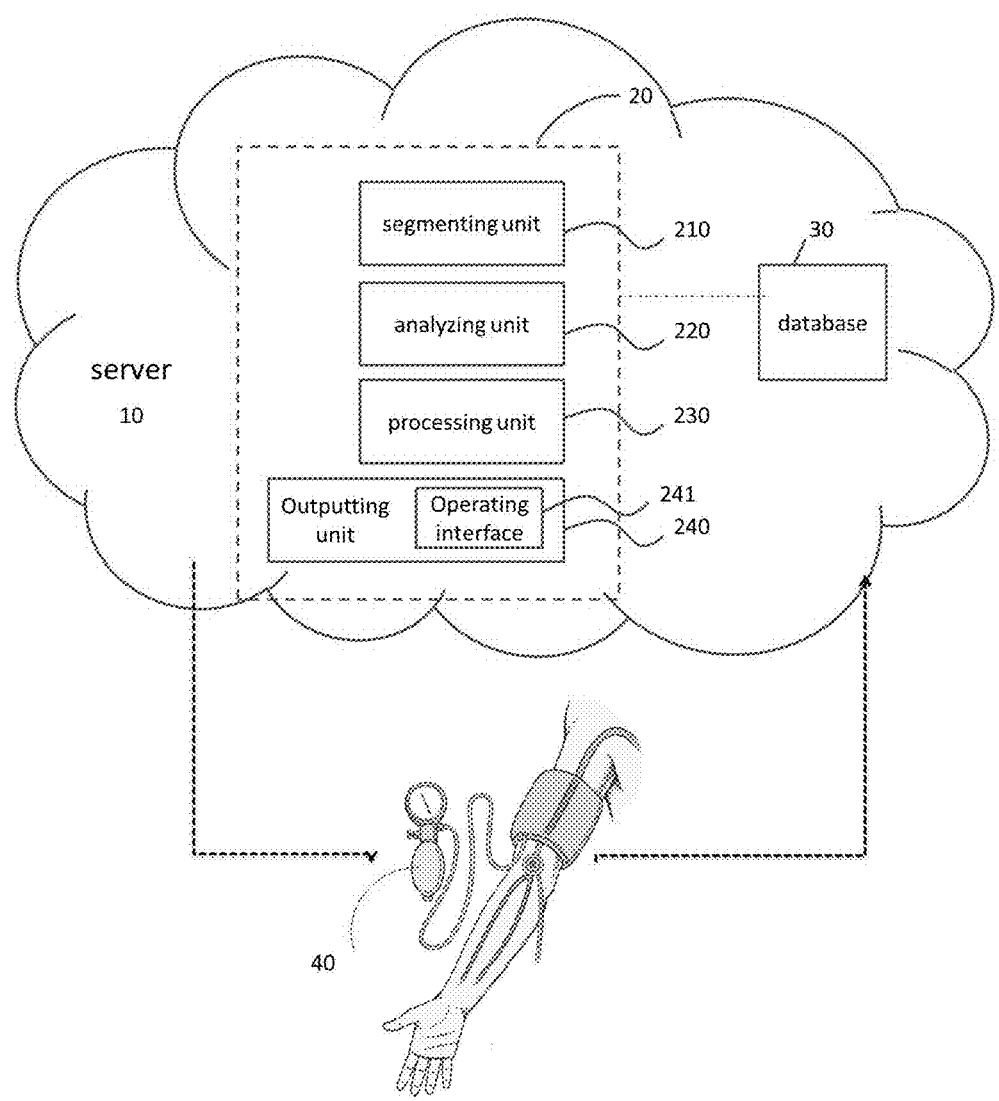
FIG. 7 shows a diagram of the diagram building system applied to a remote device (a server) in the invention.

Please refer FIG. 7. In an embodiment, the outputting device 240 includes an operating interface to adjust the time interval scales or components, which is not limited herein.

In an embodiment, the signal data TS can be a nonlinear or non-stationary data, such as physiology information of blood pressure, blood glucose, temperature, weight or electrocardiogram (ECG) signal so on, which is not limited herein.

The HHT algorithm of the analyzing processor 220 comprises an Empirical Mode Decomposition (EMD) method which is an adaptive analysis method, and can also be said a regional wave decomposition method. The EMD method can decompose any complex raw data into a plurality of different-frequency components and a non-oscillation trend by applying reasonable and concise manners. The single component is known as intrinsic mode function, and the non-oscillation trend is known as non-oscillation residue. The characteristics of the intrinsic mode functions (IMFs) include a reasonable instantaneous frequency definition which can transform every component via Hilbert transform to generate the information of instantaneous frequency and instantaneous amplitude of each component.

Then a time-frequency-energy spectrum can be obtained through mathematical computing. The time-frequency-energy spectrum includes good resolution whether in the time domain or in frequency domain. The three-dimensional distribution can reflect the essential characteristics of the signal. Frequency-amplitude spectral of two-dimensional can be obtained via the time integral of Hilbert spectrum.

HHT is a high efficient mathematical algorithm, it adjusts the baseline to analyze corresponding to changes of the data, and that is to say that HHT is adaptive to analyze or calculates the data changes over time, such as human-related physiological parameters. As a result, the diagram building system 20 of the invention can effectively and accurately decompose the data by HHT, so as to make the results produced be more informative.

That is to say, the diagram building system 20 of the invention can continuously access the various types of signals. In one embodiment, the diagram building system 20 is applied to a proximal device or a remote device to process the signal data TS, which is not limited herein.

Please refer to FIG. 7 showing a diagram of the diagram building system applied to a remote device (a server) in the invention. The device provided signal data TS can be any personal health detector 40, such as blood pressure meter, blood glucose meter, temperature meter, electrocardiogram (ECG) signal or weight meter, which is not limited herein.

The diagram building system 20 of the invention can automatically upload the relevant physiological parameter data to the server 10 via a wired connection or a wireless connection. It can provide users automatic and comprehensive analysis services by automatic acquiring, storage and analysis via network cloud. That is, the server 10 receives data directly from the personal health detector 40 and stores this data in database 30 for analysis by the diagram building system 20.

The physiological parameter data can be transferred to the segmenting processor 210 for subsequent processing via database 30. The database 30 not only can store the signal data TS, but also can store any kinds of information processed according to signal data TS, which is not limited herein.

The operating interface 241 of the outputting device 240 can adjust the time interval scales T or components to generate various three-dimensional variation visual diagrams. The three-dimensional variation visual diagram can be a three-dimensional color-level-variation visual diagram with a triangular form comprising information of different time, the different window scales and the specific frequency values, and can be displayed by an outputting interface or transferred to network cloud for users observing or inquiry, which is not limited herein.

As above mentioned, the outputting interface is formed by a command line interface (CLI) or a graphical user interface (GUI), which is not limited herein.

As above mentioned, the HHT is adaptive to analyze or calculates the data changes over time, such as human-related physiological parameters. The EMD method can decompose any complex raw data into a plurality of different single components and a non-oscillation trend as valuable references. As a result, even the signal TS stored in the database 30 is nonlinear or non-stationary, the diagram building system 20 still can effectively and accurately process and analyze these signal data, so as to make the results produced be more informative.

Figure 8:
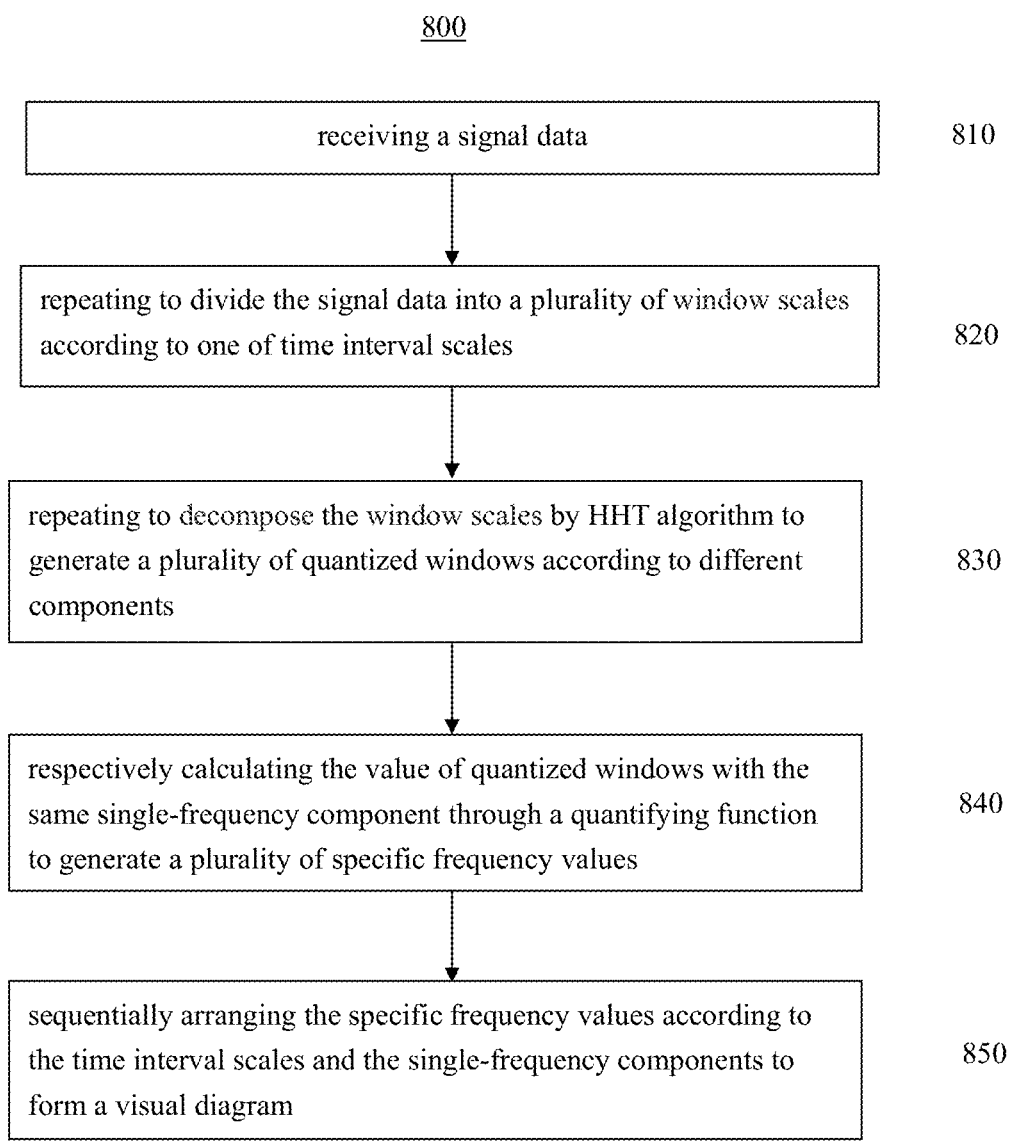
FIG. 8 shows a flow chart of the analysis method in the invention.

Please refer to FIG. 8 showing a flowchart of the diagram building method for a signal data analyzing in the invention. It is understood that the flowchart 800 of FIG. 8 provides merely an example of the many different types of functional arrangements that may be employed to implement the operation of the various components of the diagram building system 20 (FIG. 1). As an alternative, the flowchart of FIG. 8 may be viewed as depicting an example of steps of a method implemented in the diagram building system 20 according to one or more embodiments.

Although the flowchart of FIG. 8 shows a specific order of execution, it is understood that the order of execution may differ from that which is depicted. For example, the order of execution of two or more blocks may be scrambled relative to the order shown. Also, two or more blocks shown in succession in FIG. 10 may be executed concurrently or with partial concurrence. It is understood that all such variations are within the scope of the present disclosure.

Beginning with block 810, a signal data is received, wherein the signal data can be a nonlinear or non-stationary data, such as physiology information.

In block 820, the segmenting processor 210 repeats to divide the signal data into a plurality of window scales according to one of time interval scales, wherein each time interval scale is one of time periods which the signal data with.

In block 830, an analyzing processor 220 repeats to decompose the window scale by Hilbert-Huang Transform (HHT) algorithm to generate a plurality of quantized windows according to different components, wherein the components are a plurality of single-frequency components. The HHT algorithm comprises an Empirical Mode Decomposition (EMD) method. In a preferred embodiment, the components are composed of a plurality of single-frequency components, wherein the single-frequency components are a plurality of intrinsic mode functions (IMF) and a trend function.

In block 840, a reorganizing processor 230 respectively calculates the value of quantized windows with the same single-frequency component through a quantifying function to generate a plurality of specific frequency values.

In block 850, the outputting device 240 is connected to the compute device, sequentially arranges the specific frequency values according to the time interval scales and the single-frequency components to form a visual diagram, for example, a three-dimensional variation visual diagram, wherein each specific frequency value is represented by time interval scale (widow scale) and single-frequency component (time f=1/t).

Figure 9A:
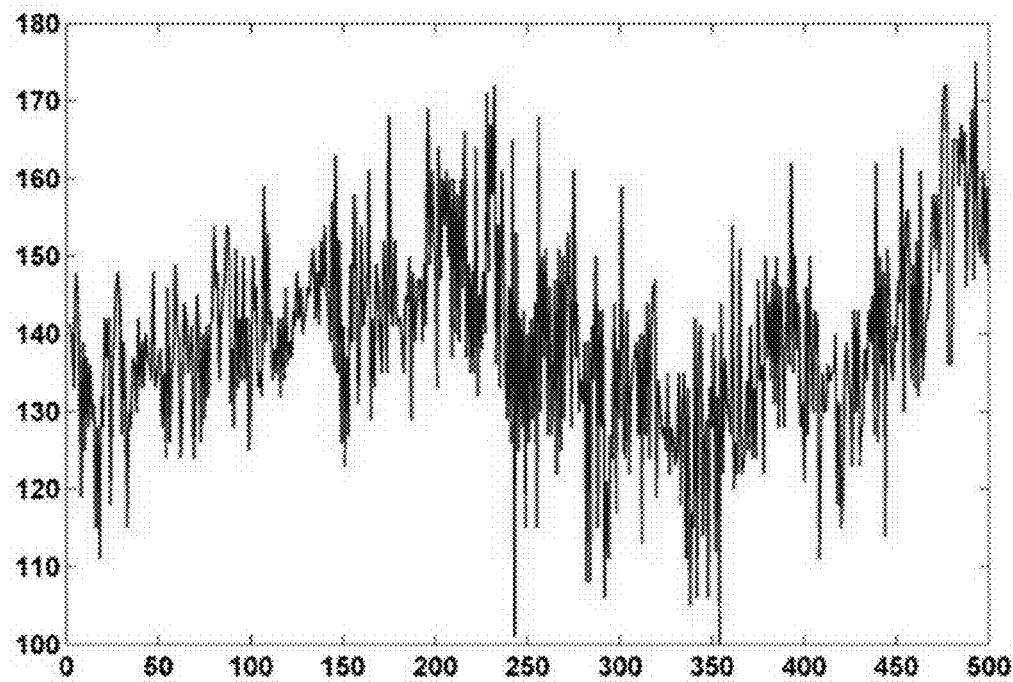
FIG. 9A shows a signal diagram of blood pressure collected for 500 days (signal TS).
Figure 9B:
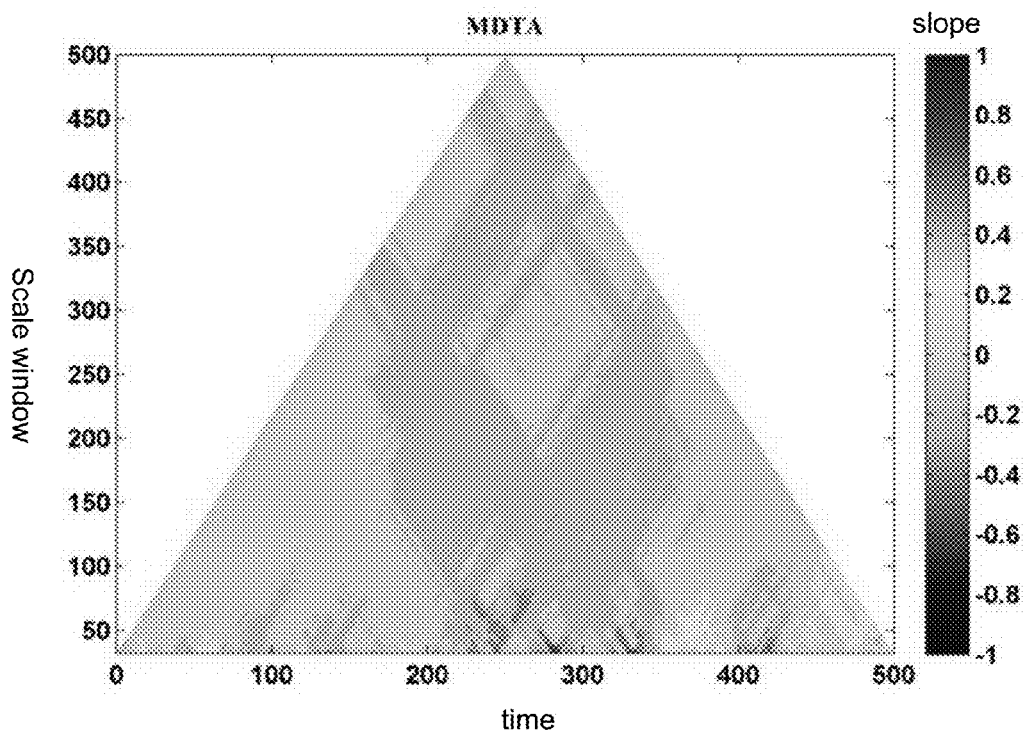
FIG. 9B shows a three-dimensional color-level-variation visual diagram with indicators of different time, different window scales and slope.
Figure 9C:
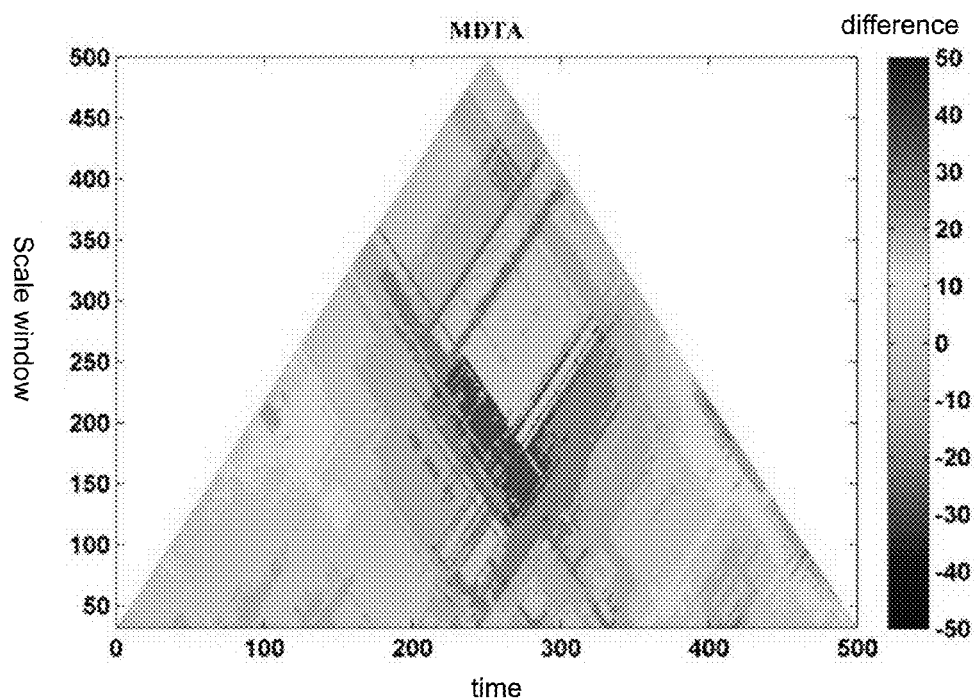
FIG. 9C shows a three-dimensional color-level-variation visual diagram with indicators of different time, different window scales and difference.
Figure 9D:
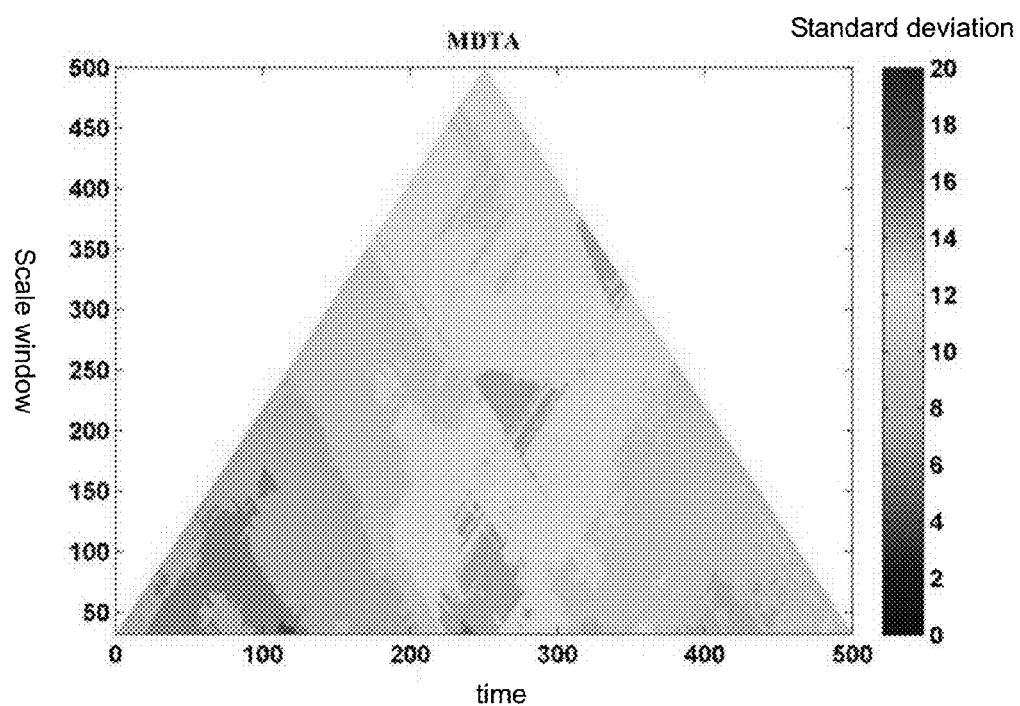
FIG. 9D shows a three-dimensional color-level-variation visual diagram with indicators of different time, different window scales and stability (standard deviation).
Figure 9E:
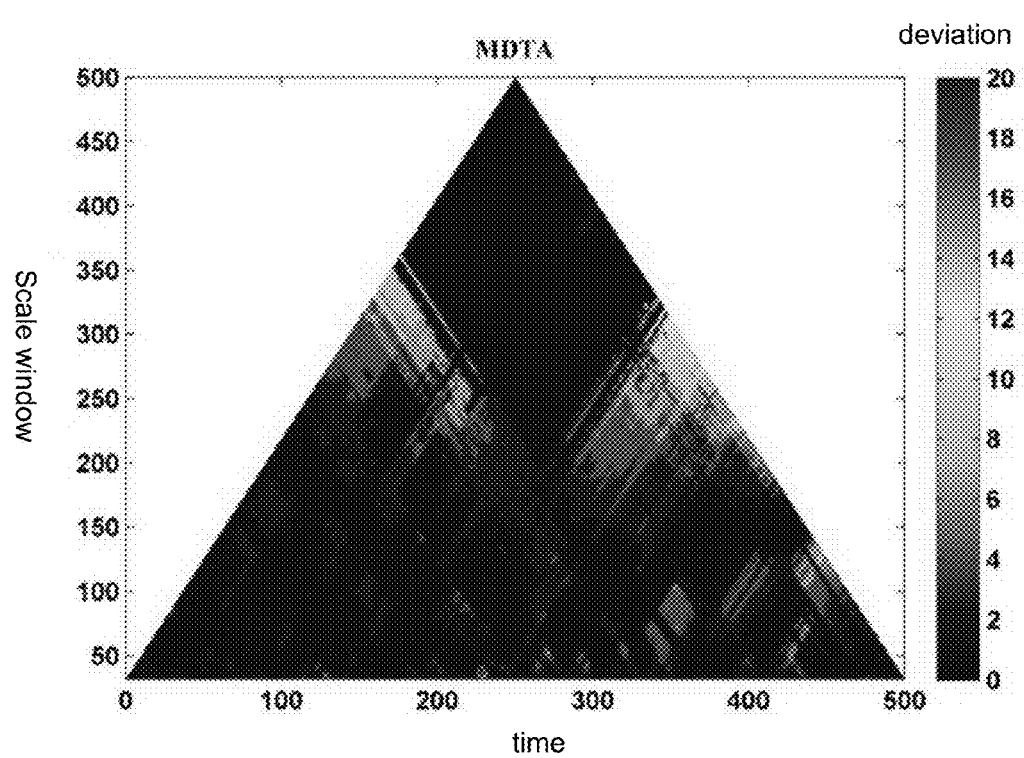
FIG. 9E shows a three-dimensional color-level-variation visual diagram with indicators of different time, different window scales and deviation.

In an embodiment, please refer to FIG. 9A to FIG. 9E. FIG. 9A shows a signal diagram of blood pressure collected for 500 days (signal TS). FIG. 9B shows a three-dimensional color-level-variation visual diagram with indicators of different time, different window scales and slope. FIG. 9C shows a three-dimensional color-level-variation visual diagram with indicators of different time, different window scales and difference. FIG. 9D shows a three-dimensional color-level-variation visual diagram with indicators of different time, different window scales and stability (standard deviation). FIG. 9E shows a three-dimensional color-level-variation visual diagram with indicators of different time, different window scales and deviation.

Figure 10A:
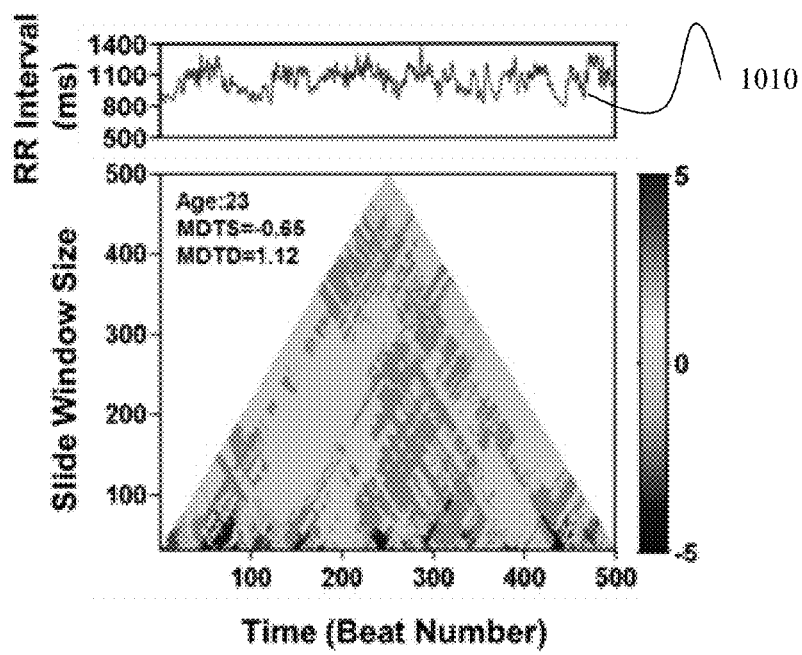
FIG. 10A shows a signal diagram of RR interval time series collected from a twenty-three olds healthy young individual and a three-dimensional color-level-variation visual diagram with indicators of different time, different window scales and slope.
Figure 10B:
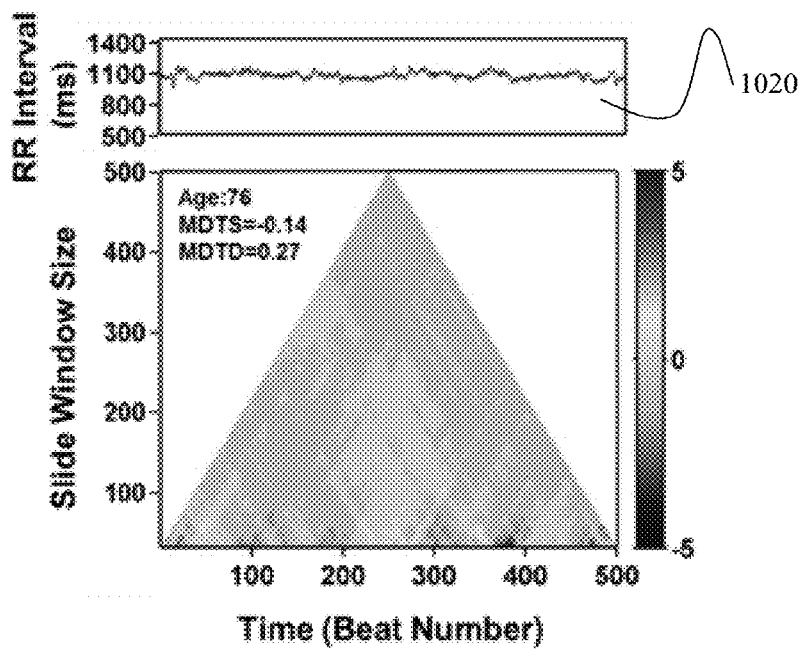
FIG. 10B shows a signal diagram of electrocardiography collected from a seventy-six olds healthy elderly individual and a three-dimensional color-level-variation visual diagram with indicators of different time, different window scales and slope.
Figure 10C:
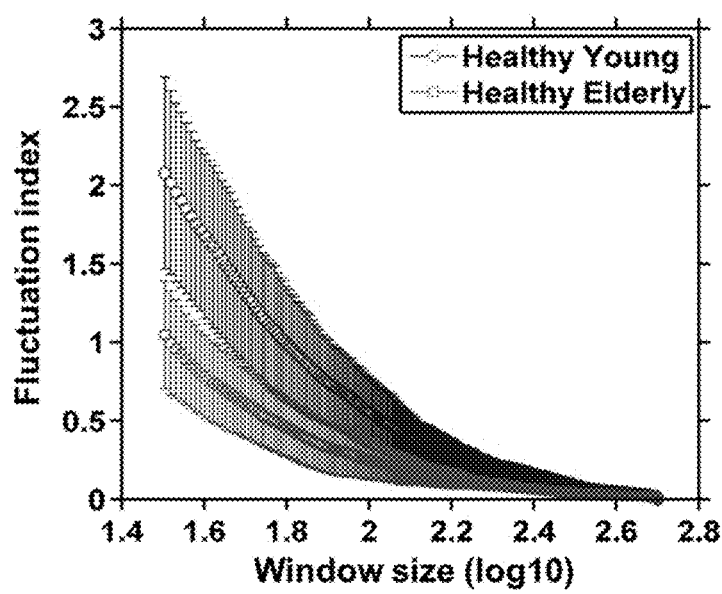
FIG. 10C shows a relationship chart between a window scale domain and a fluctuation index domain with difference.

In an embodiment, please refer to FIG. 10A to FIG. 10C. FIG. 10A shows a signal diagram of RR interval time series 1010 collected from a twenty-three olds healthy young individual and a three-dimensional color-level-variation visual diagram with indicators of different time, different window scales and slope. FIG. 10B shows a signal diagram of electrocardiography 1020 collected from a seventy-six olds healthy elderly individual and a three-dimensional color-level-variation visual diagram with indicators of different time, different window scales and slope. FIG. 10A shows a more colorful three-dimensional color-level-variation visual diagram with indicators of different time, different window scales and slope in young than FIG. 10B in elderly.

FIG. 10C shows a relationship chart between a window scale domain and a fluctuation index domain with difference. In FIG. 10C represents a healthy young person with complex and longer heart beat interval than a healthy elderly person based on a window scale domain and a fluctuation index domain. Based on analysis a heartbeat time series for twenty-three healthy young and seventy-six healthy elderly, can effectively observe and quantify with increasing age, the relevant regulatory function of physiological systems will decline.

Figure 11A:
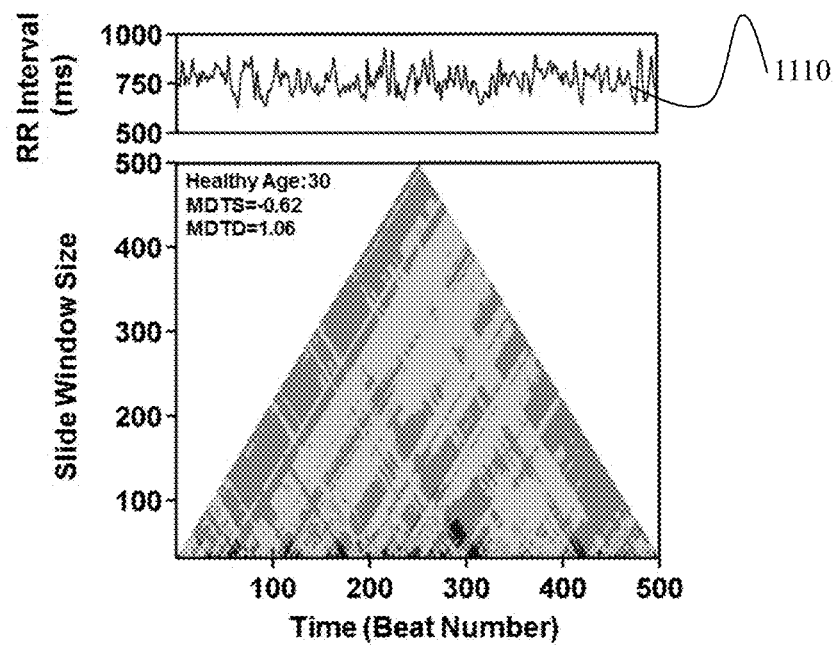
FIG. 11A shows a signal diagram of RR interval time series collected from a thirty olds healthy young individual and a three-dimensional color-level-variation visual diagram with indicators of different time, different window scales and slope.
Figure 11B:
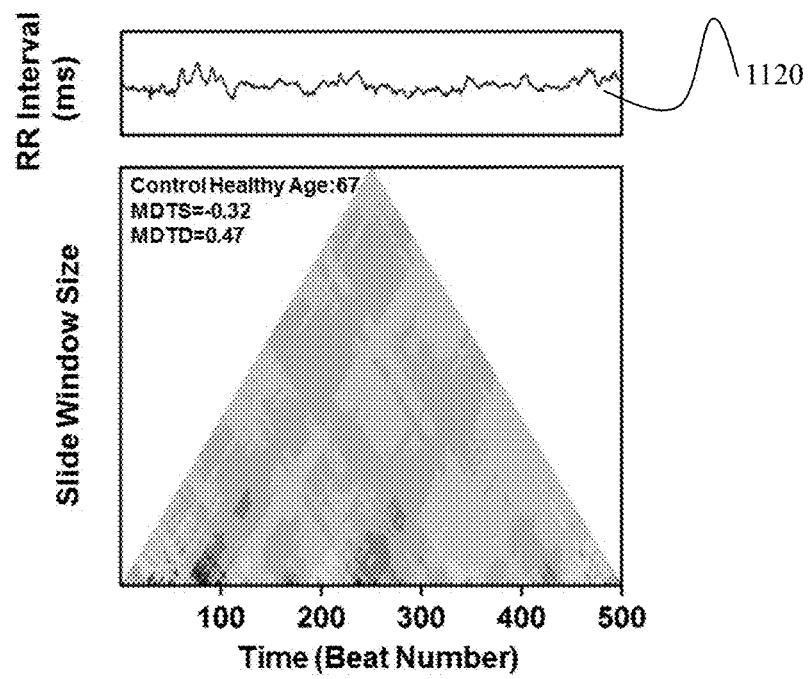
FIG. 11B shows a signal diagram of RR interval time series collected from a sixty-seven olds healthy elderly individual and a three-dimensional color-level-variation visual diagram with indicators of different time, different window scales and slope.
Figure 11C:
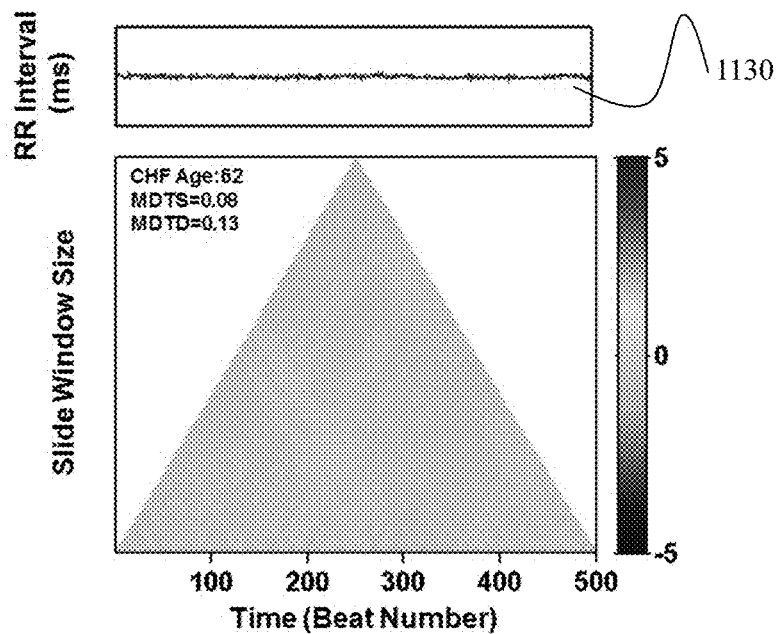
FIG. 11C shows a signal diagram of RR interval time series collected from a sixty-two olds heart failure elderly individual and a three-dimensional color-level-variation visual diagram with indicators of different time, different window scales and slope.

In an embodiment, please refer to FIG. 11A to FIG. 11D. FIG. 11A shows a signal diagram of RR interval time series 1110 collected from a thirty olds healthy young individual and a three-dimensional color-level-variation visual diagram with indicators of different time, different window scales and slope. FIG. 11B shows a signal diagram of electrocardiography 1120 collected from a sixty-seven olds healthy elderly individual and a three-dimensional color-level-variation visual diagram with indicators of different time, different window scales and slope. FIG. 11C shows a signal diagram of RR interval time series 1130 collected from a sixty-two olds heart failure elderly individual and a three-dimensional color-level-variation visual diagram with indicators of different time, different window scales and slope. FIGS. 11A and 11B show a more colorful three-dimensional color-level-variation visual diagram with indicators of different time, different window scales and slope in health than FIG. 11C in heart failure.

Figure 11D:
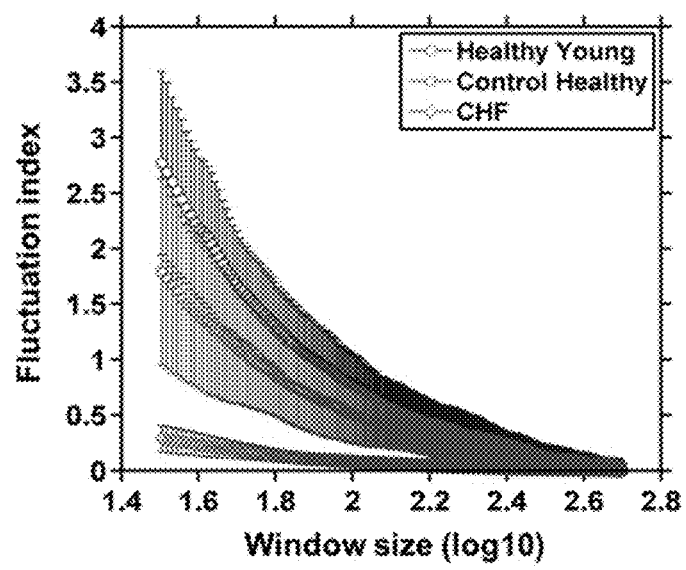
FIG. 11D shows a relationship chart between a window scale domain and a fluctuation index domain with difference.

FIG. 11D shows a relationship chart between a window scale domain and a fluctuation index domain with difference. In FIG. 11D represents a healthy young person and a healthy elderly person with complex and longer heart beat interval than a heart failure elderly person based on a window scale domain and a fluctuation index domain. Based on analysis a heartbeat time series for healthy person and heart failure person, can effectively observe and quantify with suffering from heart disease, the relevant regulatory function of physiological systems will decline.

Figure 12A:
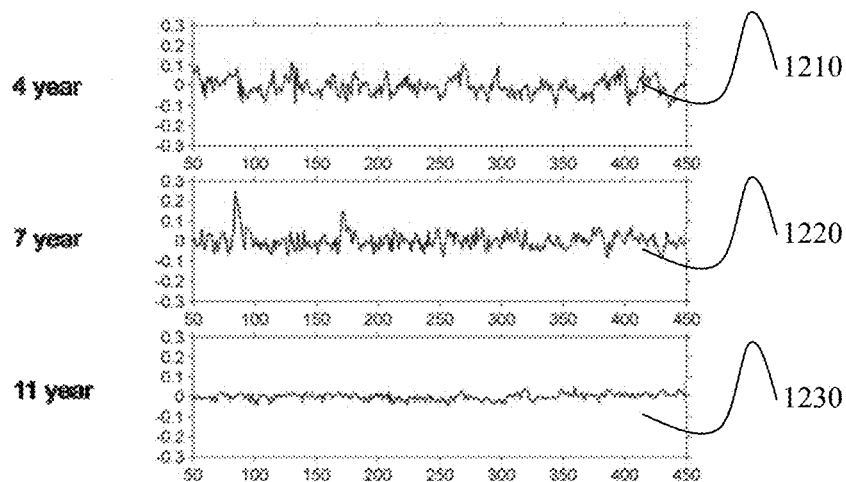
FIG. 12A shows a plurality of signal diagrams of distance between footsteps collected from different age by analysis consecutive steps.
Figure 12B:
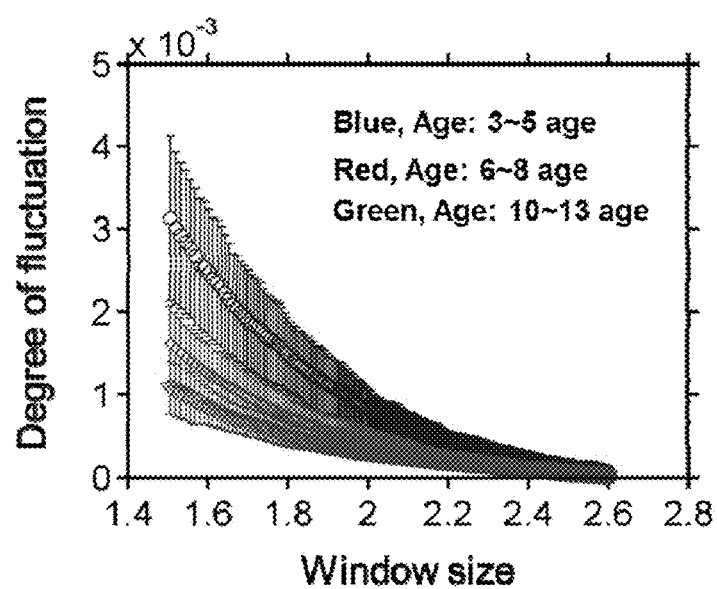
FIG. 12B shows a relationship chart between a window scale domain and a fluctuation index domain with difference.

In an embodiment, please refer to FIG. 12A to FIG. 12B. FIG. 12A shows a plurality of signal diagrams of distance between footsteps 1210, 1120, 1130 collected from different age by analysis consecutive steps. In FIG. 12A shows determining the time interval between consecutive measurements of steps. FIG. 12B shows a relationship chart between a window scale domain and a fluctuation index domain with difference. In FIG. 12B represents difference between individuals of a significant difference in age based on a window scale domain and a fluctuation index domain.

The diagram building system and method of the invention can be provided as an automated health management system through comparing the above indicators and health indicators measured. The signal data measured by personal health detectors 40 can be automatically uploaded to the server via a wired connection or a wireless connection to be either directly analyzed by the server or by the individual client. All records and information are stored and applied EMD method of Hilbert transform method to decompose the complex signal data into different components and non-oscillation trends.

The components are a plurality of intrinsic mode functions. In a preferred embodiment, the components are a plurality of single-frequency components. The non-oscillation trend is a non-oscillation residue. The intrinsic mode functions decomposed can be fluctuations information of physiological parameters in these days, weeks or months. The non-oscillation residue has ruled out the influence of the transient noise or temporary fluctuations, therefore the non-oscillation residue can be used as individual overall trend toward and changes physiological parameters, so that users can effectively get their physical condition and related information.

Although the present invention has been described in terms of specific exemplary embodiments and examples, it will be appreciated that the embodiments disclosed herein are for illustrative purposes only and various modifications and alterations might be made by those skilled in the art without departing from the spirit and scope of the invention as set forth in the following claims.

What is claimed is:

1. A diagram building system generating a visual diagram for a nonlinear or non-stationary analog signal data collected an environment during an independent time, comprising:
    an inputting device, receiving the nonlinear or non-stationary analog signal data;
    a computing device connected to the inputting device, including:
        a segmenting processor, determining a plurality of time interval scales, wherein each time interval scale is one of several time periods of the signal data, then dividing the signal data of each time interval scale into a plurality of window scales according to a time interval scales selection;
        an analyzing processor, repeating to decompose each of the window scales by Hilbert-Huang Transform (HHT) algorithm to generate a plurality of quantized windows according to different components, wherein the components are a plurality of single-frequency components; and
        a reorganizing processor, selecting the quantized windows from each time interval scale and dividing with each corresponding different component to generate a plurality of specific frequency values through a quantifying function;
    the computing device obtaining the specific frequency values of the time interval scales by dividing according to different time periods, then selecting at least two colors, expressing a minimum and a maximum of the specific frequency values by two colors of the at least two colors, and expressing other intensities of a specific frequency values by a plurality of other colors in different mixing ratios of the at least two colors; and
    an outputting device connected to the computing device, sequentially arranging the at least two colors and the other colors according to the time interval scales and the different components of the specific frequency values on a coordinate map that shows a relationship between a window scale domain and a time domain of a specific frequency value to form the visual diagram.

2. The diagram building system according to claim 1, wherein the HHT algorithm comprises an Empirical Mode Decomposition (EMD) method.

3. The diagram building system according to claim 1, wherein the single-frequency components are a plurality of intrinsic mode functions (IMF) and a trend function.

4. The diagram building system according to claim 1, wherein the quantifying function is a standard deviation function, a value difference function, a value slope function or a fluctuation index function.

5. The diagram building system according to claim 1, wherein the relationship of specific frequency value is a three-dimensional color-level-variation visual diagram with a triangular form.

6. The diagram building system according to claim 1, wherein the visual diagram is the relationship between a window scale domain and a fluctuation index domain.

7. The diagram building system according to claim 1, wherein the signal data is a nonlinear or non-stationary data.

8. The diagram building system according to claim 7, wherein the nonlinear or non-stationary data is physiology information.

9. The diagram building system according to claim 1, the compute device is a remote device or a proximal device.

10. The diagram building system according to claim 1, the outputting device is a graphical user interface.

11. A diagram building method for generating a visual diagram for a nonlinear or non-stationary analog signal data collected from a phenomenon variety during an independent time, comprising:
   a. receiving the nonlinear or non-stationary analog signal data;
   b. determining a plurality of time interval scales, wherein each time interval scale is one of several time periods of the signal data;
   c. dividing the signal data into a plurality of window scales according to one of the time interval scales selections;
   d. repeating to decompose each of the window scales by an HHT algorithm to generate a plurality of quantized windows according to different components, wherein the components are a plurality of single-frequency components;
   e. respectively selecting the quantized windows from a same time interval scale dividing with the same single-frequency component to generate a plurality of specific frequency values through a quantifying function;
   f. repeating step c to step e for each of the time interval scales, obtaining specific frequency values of the time interval scales divided according to different time periods;
   g. selecting at least two colors, expressing a minimum and a maximum of the specific frequency values by two colors of the at least two colors, and expressing other intensities of a specific frequency values by a plurality of other colors in different mixing ratios of the at least two colors; and
   h. sequentially arranging the two colors and the other colors according to the time interval scales and the single-frequency components of the specific frequency values on a coordinate map that shows a relationship between a window scale domain and a time domain of a specific frequency value to form the visual diagram.

* * * * *